United States Patent
Gagel et al.

(10) Patent No.: US 10,010,289 B2
(45) Date of Patent: Jul. 3, 2018

(54) METHOD AND DEVICE FOR MONITORING AN EXTRACORPOREAL BLOOD TREATMENT OF A PATIENT

(71) Applicant: Fresenius Medical Care Deutschland GmbH, Bad Homburg (DE)

(72) Inventors: Alfred Gagel, Litzendorf (DE); Andreas Maierhofer, Schweinfurt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 703 days.

(21) Appl. No.: 13/917,944

(22) Filed: Jun. 14, 2013

(65) Prior Publication Data
US 2014/0046150 A1 Feb. 13, 2014

Related U.S. Application Data

(60) Provisional application No. 61/660,016, filed on Jun. 15, 2012.

(30) Foreign Application Priority Data

Jun. 15, 2012 (EP) .................................. 12172251

(51) Int. Cl.
*A61B 5/1455* (2006.01)
*A61B 5/00* (2006.01)
(Continued)

(52) U.S. Cl.
CPC .......... *A61B 5/4848* (2013.01); *A61B 5/0071* (2013.01); *A61B 5/05* (2013.01);
(Continued)

(58) Field of Classification Search
None
See application file for complete search history.

(56) References Cited

U.S. PATENT DOCUMENTS 4,496,722 A * 1/1985 Gallop ............. A61K 47/48061
544/69
5,626,134 A 5/1997 Zuckerman
(Continued)

FOREIGN PATENT DOCUMENTS

CN 101098721 1/2008
CN 101479595 7/2009
(Continued)

OTHER PUBLICATIONS

Smutzer et al. "A fluorescent sterol probe study of human serum low-density lipoproteins" Biochimica et Biophysica Act, vol. 958, No. 3, Feb. 19, 1988, pp. 323-333.
(Continued)

*Primary Examiner* — Eric Winakur
*Assistant Examiner* — Marjan Fardanesh
(74) *Attorney, Agent, or Firm* — Jacobson Holman, PLLC.

(57) ABSTRACT

The present invention pertains to Method for monitoring a dialysis treatment of a patient, preferably for monitoring a haemodialysis, haemodiafiltration and/or peritoneal dialysis treatment of a patient, the method including the steps of:
- irradiating a sample of a dialysis fluid used in the dialysis treatment with linearly polarized irradiation light;
- detecting the intensity of the fluorescence light emitted by the dialysis fluid in a first polarization plane;
- detecting the intensity of the fluorescence light emitted by the dialysis fluid in a second polarization plane which is different from the first polarization plane;
- determining the anisotropy of the fluorescence light emitted by the dialysis fluid; and
- determining the concentration of at least one fluorophore in the dialysis fluid on the basis of both, the determined anisotropy and the intensity of the fluorescence light emitted by the dialysis fluid.

20 Claims, 5 Drawing Sheets

(51) Int. Cl.
    *A61B 5/145*     (2006.01)
    *A61M 1/16*     (2006.01)
    *A61B 5/05*     (2006.01)
    *A61M 1/28*     (2006.01)
    *A61M 1/34*     (2006.01)

(52) U.S. Cl.
    CPC ........ *A61B 5/1455* (2013.01); *A61B 5/14546* (2013.01); *A61B 5/14558* (2013.01); *A61B 5/4836* (2013.01); *A61B 5/6866* (2013.01); *A61B 5/7225* (2013.01); *A61M 1/16* (2013.01); *A61M 1/1609* (2014.02); *A61M 1/1619* (2014.02); *A61M 1/28* (2013.01); *A61M 1/3406* (2014.02); *A61M 2205/3306* (2013.01)

(56) References Cited

U.S. PATENT DOCUMENTS

| | | | |
|---|---|---|---|
| 6,590,651 B1* | 7/2003 | Bambot | A61B 5/0071 356/338 |
| 2008/0158544 A1 | 7/2008 | Womble et al. | |
| 2008/0225265 A1 | 9/2008 | Pusey et al. | |
| 2011/0188043 A1* | 8/2011 | Davidov | G01N 21/553 356/445 |

FOREIGN PATENT DOCUMENTS

| | | |
|---|---|---|
| JP | H09512446 | 12/1997 |
| JP | 2002098638 | 4/2002 |
| JP | 2005515845 | 6/2005 |
| WO | WO 2010/091826 | 8/2010 |
| WO | WO 2011154514 | 12/2011 |

OTHER PUBLICATIONS

Shaw et al. "Resonance energy transfer and ligand binding studies on pH-induced folded states of human serum albumin." Journal of Photochemistry and Photobiology B: Biology, vol. 90, No. 3, Jan. 9, 2008, pp. 187-197.

Yamasaki et al. "Characterization of site I of human serum albumin using spectroscopic analyses: Locational relations between regions Ib and Ic of site I," Journal of Pharmaceutical Sciences, vol. 93, No. 12, Dec. 2004, pp. 3004-3012.

* cited by examiner

METHOD AND DEVICE FOR MONITORING AN EXTRACORPOREAL BLOOD TREATMENT OF A PATIENT

TECHNICAL FIELD

The present invention pertains to a method and a device for monitoring an extracorporeal blood treatment of a patient, preferably for monitoring a dialysis, haemodialysis, haemodiafiltration, haemofiltration and/or peritoneal dialysis treatment of a patient.

TECHNICAL BACKGROUND

Dialysis is one of the most commonly known and used extracorporeal blood treatment methods and is intended to replace the function of the kidneys when a renal failure of the kidneys occurred in a patient.

When the kidneys fail, dialyzing a patient is necessary to remove waste products such as urea, creatinine and uremic toxins from the blood of the patient. Furthermore, during dialysis, excess water and other substances which are usually eliminated by urine are removed from the body of the patient. The most commonly used method of dialysis is hemodialysis in which the blood of the patient flows along a dialyzing membrane, wherein on the other side of this dialyzing membrane a dialyzing liquid is provided. Accordingly, blood and dialyzing liquid are separated by the porous membrane.

Through this membrane, the substances which are to be removed from the blood of the patient diffuse because of a concentration gradient between blood and the dialyzing liquid. Larger molecules, whose diffusion velocity is very slow, can also be transported convectively by means of a liquid flow from the blood side to the dialysis liquid side of the membrane.

The dialysis liquid is prepared to have a concentration which provides for a concentration gradient from the blood side to the dialysis liquid side for certain substances, but not necessarily for all substances. In fact, the removal of urea and creatinine as well as other waste products in the human body is desired but, for example, the removal or change of concentration of electrolytes such as potassium, sodium or bicarbonate is not at all desired but is considered harmful. Accordingly, the dialysis liquid typically contains a concentration of the electrolytes which resembles the concentration of electrolytes in the blood plasma of the patient such that a concentration gradient is not present for these substances.

Besides the hemodialysis, peritoneal dialysis is another dialysis method which also uses a membrane and a dialysis liquid in order to achieve a diffusion of the waste product through the membrane into the dialysis liquid. The membrane, however, is a natural membrane namely the peritoneum and the dialysis liquid is introduced directly into the abdominal cavity.

During dialysis, the elimination of excess water and small molecular uremic substances such as urea and creatinine is typically no problem, larger molecules, however, are more difficult to remove through the porous membrane. In order to tackle this, specific high flux dialysis membranes are provided in combination with highly convective methods, such as hemodiafiltration. This results in improvements in the clearance of molecules of molecular masses over 1 kDa, which is the range of the so-called middle-sized molecules. In hemodiafiltration, a diffusion method using the dialysis liquid in the form as described above is combined with hemofiltration, in which the blood of a patient is subjected to a pressure gradient across a filter. Accordingly, the filtration process along the pressure gradient leads to an increased liquid flow and is, thus, considered a highly convective method which enables the removal of a considerable portion of middle-sized molecules. However, due to the pressure gradient, water as well as electrolytes and sugars are also removed from the blood of the patient at a high rate such that these blood constituents have to be replaced by means of the infusion of a replacement fluid.

The introduction of the high flux dialysis membranes in combination with highly convective methods improves the clearance for middle-sized and larger molecules.

Larger molecules are typically proteins, wherein, for example, beta2-microglobulin has a size of about 11 kDa, wherein this molecule may induce an amyloidosis if not sufficiently removed. Smaller molecules which are toxic may also be difficult to dialyze if the molecules are bound to proteins. For example, uremic toxins which are bound to proteins are p-cresyl sulfate and indoxyl sulfate.

Accordingly, it is desired to have pore sizes in the dialysis membranes which are sufficiently large to let through these middle-sized molecules. On the other hand, the pore size of the membrane cannot be extended infinitely, because the higher the pore size of the membrane, the higher the risk that vital blood components are likewise lost. Accordingly, the permeability of the membrane is typically limited to sizes of around 60 kDa. However, this value is just slightly below the molecular mass of human plasma albumin which has a size of about 66 kDa. In practice, clinically significant losses of albumin may happen wherein these losses significantly depend on the respective parameters of the method, such as the respective pressures and the respective concentrations in the dialysis liquid. In particular, a high flux membrane in combination with the pressure gradient applied during hemofiltration increases the clearance of human albumin. Another reason for the loss of human albumin may be the multiple use of the membranes because the cleaning of the membrane which is necessary between different treatments tends to increase the sizes of the pores in the membrane. This shifts the permeability of the membrane towards higher molecules. Accordingly, even under normal conditions in normal hemodialysis, human serum albumin may penetrate through the membrane.

It goes without saying that in the case of the peritoneal dialysis the sizes of the pores of the membrane cannot be influenced but are given by the condition of the peritoneum of the respective patient. However, a loss of human albumin into the dialysis liquid may nevertheless take place once the peritoneum has been impaired, for example, by an inflammation.

In order to determine the clearance of an analyte during dialysis, a Raman spectroscopy method is disclosed in US 2008/0158544 A1, wherein the Raman spectral measurements are carried out on the blood after it has passed the dialyzer in order to utilize the unique Raman spectroscopic signature of one or more analytes, e.g., urea, to identify and quantify such analytes against a whole blood background.

WO 2010/091826 A1 relates to an apparatus for the extracorporeal treatment of blood, wherein the absorption of electromagnetic radiation in the dialysis liquid is measured in order to determine the Kt/V value, namely the clearance K of the volume flow of the clean substances, wherein t is the treatment time and V the distribution volume of the patient. In renal replacement therapy, urea is typically used as a marker substance for measuring treatment efficiency of uric acid, such that K is the uric acid clearance and V the urea distribution volume of the patient, which corresponds, in principle, to the body water of the patient. However, by measuring the total absorption, in general the clearance for a specific molecule cannot be determined.

Accordingly, it is desired to monitor the loss of human albumin during dialysis treatments in order to alert the medical personnel of this condition, such that the treatment can be adjusted or even to automatically adjust or even interrupt the treatment in case of excessive loss of albumin.

Furthermore, other proteins such as the above-mentioned middle molecules (proteins with sizes of smaller than 66 kDa) as well as further smaller molecular substances such as p-cresyl sulfate, indoxyl sulfate or phenyl are also to be determined as to their clearance because these substances are toxic.

SUMMARY OF THE INVENTION

Accordingly, it is an object of the present invention to provide a method and an apparatus for monitoring an extracorporeal blood treatment of a patient.

This objective is solved by means of the method according to claim 1. Advantageous embodiments can be taken from the dependent claims.

Accordingly, the method for monitoring an extracorporeal blood treatment of a patient, preferably for monitoring a dialysis, haemodialysis, haemodiafiltration, haemofiltration and/or peritoneal dialysis treatment of a patient, includes the steps of irradiating a sample of a fluid used in the extracorporeal blood treatment with linearly polarized irradiation light, detecting the intensity of the fluorescence light emitted by the sample of the fluid in a first polarization plane, detecting the intensity of the fluorescence light emitted by the sample of the fluid in a second polarization plane which is different from the first polarization plane, determining the anisotropy of the fluorescence light emitted by the sample of the fluid, and determining the concentration of at least one fluorophore in the sample of the fluid on the basis of both, the determined anisotropy and the intensity of the fluorescence light emitted by the sample of the fluid.

By means of determining the concentrations of the respective fluorophores in the sample of the fluid on the basis of the measured anisotropy and the intensity of the polarized fluorescence light, it is possible to distinguish between the fluorescence signals of several fluorescence active substances in the sample of the fluid. In fact, by using the anisotropy for determining the individual concentrations of the individual fluorophor in the sample of the fluid, it becomes possible to determine the individual concentration of the respective fluorophor in the sample of the fluid because the anisotropy is different for every fluorophore.

The fluid used in the extracorporeal blood treatment may be a dialysis fluid in case of the dialysis, haemodialysis, haemodiafiltration and/or peritoneal dialysis treatments of a patient or an ultrafiltrate in case of a haemofiltration treatment of a patient.

By means of using this variant of fluorescence spectroscopy, the performance e.g. of convective dialysis treatments can be determined online during the treatment. The performance can be determined for example by analyzing the contents of the dialysis fluid. If the clearance of specific molecules is below a certain limit or if substances such as human albumin are removed from the plasma of the patient in unacceptable quantities, the treatment process may be adjusted automatically by the treatment apparatus and/or an alarm can be issued.

Preferably, the first polarization plane and the second polarization plane are oriented perpendicular with respect to one another and the anisotropy A is determined on the basis of the following equation $$A = \frac{I_{vv} - G * I_{vh}}{I_{vv} + 2 * G * I_{vh}}$$

where $I_{vv}$ is the intensity of the detected fluorescence light in the vertical polarization plane, $I_{vh}$ is the intensity of the detected fluorescence light in the horizontal polarization plane, and G is an apparatus constant compensating differences in the sensitivities of the apparatus when detecting intensities in the first and second polarization planes. The anisotropy can be used to determine the fluorophore exactly because different fluorophores show different anisotropies.

In a further preferred embodiment the intensity of the fluorescence light is detected at a predetermined detection wavelength when illuminating the sample at a predetermined irradiation wavelength, and the anisotropy is used to determine the individual fluorophore, and the intensity of the fluorescence light is used to determine the concentration of this individual fluorophore, wherein preferably the anisotropy of specific individual fluorphores is known.

Preferably, the concentrations of at least two fluorophores present in the sample of the fluid are determined on the basis of the following equation of the total anisotropy $A_{ges}$ of the summed spectra:

$$A_{ges} = \sum_i f_i * A_i$$

$$\text{wherein } f_i = \frac{S_i}{S_{ges}} = \frac{I_{vv,i} + 2 * G * I_{vh,i}}{I_{vv,ges} + 2 * G * I_{vh,ges}}$$

and wherein $A_{ges}$ is the total anisotropy of the summed spectra, $A_i$ is the anisotropy of the $i^{th}$ fluorophor, $f_i$ is the intensity fraction of the $i^{th}$ fluorophore with respect to the total intensity, $S_i$ is the total intensity of the physical radiation of the $i^{th}$ fluorophore, $S_{ges}$ is the total intensity of the physical radiation of all fluorophors, $I_{vh,i}$ is the detected horizontal fluorescence intensity of the $i^{th}$ fluorophor, $I_{vv,i}$ is the detected vertical fluorescence intensity of the $i^{th}$ fluorophor, and i is the index over all fluorophors, and wherein the anisotropy $A_i$ of the $i^{th}$ fluorophor is preferably known. On this basis, it becomes possible to determine the concentrations of at least two fluorophores in the sample of the fluid on the basis of the detected fluorescence light. In other words, it becomes possible to distinguish between different individual fluorophores in the sample of the fluid, for example in the dialysis fluid or in the ultrafiltrate.

Furthermore, it is preferred to continuously irradiate the sample of the fluid and to carry out the detection continuously. Variations in the concentrations of different samples of the fluid can be observed in this manner easily. The term "continuous" it is understood to include short interceptions of the measurement process during the extracorporeal blood treatment of the patient, for example during set-up or adjustment procedures of an extracorporeal blood treatment apparatus.

Preferably, the concentration of a fluorophore is directly determined on the basis of the total anisotropy, wherein preferably the concentration of albumin is determined on the basis of the total anisotropy. This is particularly helpful if the contribution of the fluorophore to the total anisotropy is significant.

In a preferred embodiment, the concentration of a fluorophore, preferably the concentration of human albumin, is determined directly on the basis of the vertical and horizontal intensities of the detected fluorescence light. This, again, is particularly suitable when the contribution of the fluorophore to the total anisotropy of the dialysis fluid is significant. On the basis of this method, the determination of the concentration is very easy to carry out.

In a further preferred embodiment, the sample of the fluid is irradiated with pulsed and linearly polarized irradiation light and the detection of the fluorescence light in the first and second polarization planes is carried out in a time-resolved fashion and the anisotropy is determined as $$A = A_0 * e^{-t/\theta}$$

where $\theta$ is the rotation correlation time, which is a characteristic time constant describing the time period within which the axis of the transition dipole moments are oriented diffusely by means of rotation of the molecules, and $A_0$ is the anisotropy at the time point t=0, before depolarizing effects apply. The rotation correlation time $\theta$ of the anisotropy can be used to determine the substance of the fluorophore because every fluorophore has a different rotation correlation time $\theta$.

Preferably, the rotation correlation time $\theta$ is varied by means of varying the temperature of the sample of the fluid, by varying the viscosity of the sample of the fluid, and/or by applying external magnetic and/or electrical fields in order to further identify the fluorophore on the basis of the behavior of the rotation correlation time $\theta$.

In a further preferred method, the total fluorescence intensity is increased by aligning the transition dipole moments of the sample by application of external electrical and/or magnetic fields. The application of external fields aids in increasing the detected intensities and, thus, improves the signal to noise ratio.

Preferably, a matrix decomposition of the measured anisotropy spectrum is carried out and a comparison to known anisotropy spectra of known substances is carried out in order to determine on the basis of the respective intensities of the known substances their respective concentrations. On this basis, it becomes possible to analyze even complex superpositions of fluorescence spectra as to the actual composition of the sample of the liquid.

It is preferred to carry out a reference measurement on fresh dialysis fluid in a dialysis, haemodialysis, haemodiafiltration and/or peritoneal dialysis treatment of a patient such that the contribution of contaminations of the initial dialysis fluid to the readings taken from the used dialysis fluid can be eliminated. The method preferably uses the steps of irradiating a sample of fresh dialysis fluid to be used in the extracorporeal blood treatment with linearly polarized irradiation light; detecting the intensity of the fluorescence light emitted by the sample of the fresh dialysis fluid in a first polarization plane; detecting the intensity of the fluorescence light emitted by the sample of the fresh dialysis fluid in a second polarization plane which is different from the first polarization plane; determining the anisotropy of the fluorescence light emitted by the sample of the fresh dialysis fluid; and determining the concentration of at least one fluorophore in the sample of the fresh dialysis fluid on the basis of both, the determined anisotropy and the intensity of the fluorescence light emitted by the fluid.

In another preferred method, the concentration of human albumin in the sample is determined on the basis of a subtraction of the detected horizontal intensity minus the detected vertical intensity.

The above-mentioned objective is also met by a device with the features of claim 15. Preferred embodiments can be taken from the dependent claims.

Accordingly, the device for monitoring an extracorporeal blood treatment of a patient, preferably for monitoring a dialysis, haemodialysis, haemodiafiltration, haemoflitration and/or peritoneal dialysis treatment of a patient, includes an irradiation light source for irradiating a sample of a fluid used in the dialysis treatment with linearly polarized light, and a detector for detecting the intensity of the fluorescence light emitted by the sample of the fluid in a first polarization plane and in a second polarization plane which is different from the first polarization plane, wherein an analysis unit is present for determining the anisotropy of the fluorescence light emitted by the sample of the fluid and for determining the concentration of at least one fluorophore in the sample of the fluid on the basis of the determined anisotropy and the intensity of the fluorescence light emitted by the sample of the fluid.

Preferably, at least two polarizers with polarization planes aligned under an angle are provided between the sample of the fluid and a detector for detecting the intensity of the fluorescence light, wherein a movable shutter is present in the light path to alternately cover either of the two polarizers to alternately detect the intensities of the fluorescence light in the two polarization planes. By means of the provision of the two polarizers, a setup can be provided which avoids the movement of the optical parts and, thus, enables reliable measurements.

Preferably, a rotatable shutter may be present in the light path of the transmitted light of the light source through the sample of the fluid such that the intensity of the transmitted light as well as the intensities of the fluorescence light in at least two different polarization planes can be detected by means of the single detector.

Furthermore, in an alternative, a first detector with an associated polarizer with a first polarization plane and a second detector with a second polarization plane different from the first polarization plane are arranged on opposite sides of the sample of the fluid to detect fluorescence light of a first and a second polarization plane simultaneously.

Preferably, a third detector is present collinearly with the irradiation light and such that the sample of fluid is placed between the detector and the irradiation light source to detect the transmission intensity.

The device preferably is configured to perform the method outlined above.

BRIEF DESCRIPTION OF THE DRAWINGS

The present disclosure will be more readily appreciated by reference to the following detailed description when being considered in connection with the accompanying drawings in which.

DETAILED DESCRIPTION OF PREFERRED EMBODIMENTS

Figure 1:
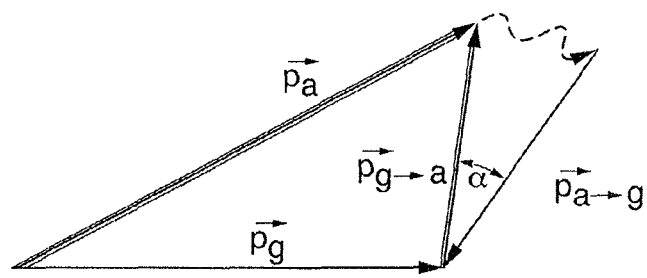
FIG. 1 shows a schematic diagram of the dipole moments of a molecule as well as the transition dipole moment of the molecule.

In the following, the invention will be explained in more detail with reference to the accompanying Figures. In the Figures, like elements are denoted by identical reference numerals and repeated description thereof may be omitted in order to avoid redundancies.

It is an objective of the present invention to monitor the clearance of certain molecules in an extracorporeal blood treatment and, at the same time, make sure that important molecules such as human albumin are not removed in excessive quantities.

In the following, the method is elaborated on the basis of a dialysis treatment. However, it is not intended to be limited to dialysis treatments only but is rather intended to be used in all other extracorporeal blood treatments such as for monitoring a dialysis, haemodialysis, haemodiafiltration, haemofiltration and/or peritoneal dialysis treatment of a patient.

In order to meet this objective, the concentration of albumin as well as the concentrations of a fraction of the so-called middle molecules, namely proteins with a size smaller than 66 kDa, must be measurable individually. Furthermore, in the used dialysate additional small molecular substances such as indoxy sulfate, p-cresol and phenol are present which are also fluorescence active.

Unfortunately, the emission spectra of the individual fluorophors which are of interest for pathological analysis widely overlap for a specific irradiation wavelength and are also present in the identical UV ranges. In addition to this inconvenience, the fluorescence spectra of the molecules mentioned before are relatively wide such that a deconvolution of the measured spectra is difficult or can only be carried out with large measurement errors. Accordingly, on the basis of the common fluorescence spectroscopy it is not possible to determine the exact concentration or exact proportion of an individual substance in a dialysis fluid and, thus, it is not possible to provide a reliable quantitative determination of the concentrations.

By means of using the anisotropy as suggested in the present invention, this problem can be overcome. The effect connected herewith is termed photo selection according to which the emitted fluorescence light of a sample shows anisotropy of the emitted fluorescence light after excitation of the sample with linearly polarized light.

Generally, when an atom or a molecule electronically absorbs a photon, an electron is lifted to a higher atomic or molecular orbit. Due to this shift of the electronic structure, a new spatial distribution of the charges is present such that the electronic dipole moment of the absorbing atom or molecule is typically changed.

The transition dipole moment is defined by the electric dipole moment which is associated with a transition between the ground state and the excited state of the respective atom or molecule. The direction of the vector of the transition dipole moment corresponds to the polarization plane of the transition which determines how the molecule will interact with an electromagnetic wave of a given polarization. The square of the magnitude of the transition dipole moment is the strength of the interaction on the basis of the distribution of the charges within the molecule.

FIG. 1 shows in a simplified representation the transition dipole moment $p_{a \to g}$ when the respective molecule is excited from the electronic dipole moment of the ground state $p_g$ into the elevated state $p_a$ by excitation of the molecule by means of the excitation energy field vector $p_{g \to a}$. Furthermore, it is shown that the molecule typically relaxes by means of internal processes (so-called inner conversion which is typically due to vibrational processes in the molecule), before it relaxes from the excited state into the ground state via the transition dipole moment $p_{a \to g}$. Due to the internal relaxation processes the vector of the transition dipole moment $p_{a \to g}$ is typically shifted by means of the angle α with respect to the excitation vector $p_{g \to a}$.

The transition dipole moment is determined by the structure of each molecule and moves together with the molecule but the relative alignment with respect to the molecule remains fixed.

As can be easily appreciated, the probability for absorption is the highest when the orientation of the electromagnetic wave of a given polarization, or more precisely its field vector, is collinear with the transition dipole moment $p_{a \to g}$. Accordingly, if linearly polarized light is used to excite a molecule in the sample of dialysis fluid, the probability of exciting the molecule by means of the linearly polarized light is the highest for molecules which fulfill the collinearity requirements by chance. This process is termed photo selection because the molecules are excited which are—by chance—arranged in a specific spatial relationship to the polarization plane of the irradiation light.

In addition, the orientation of the transition dipole moment $p_{a \to g}$ determines the polarization of the emitted fluorescence light when the transition from the excited state to the ground state is carried out by means of the emission of a photon (of course, relaxation without the emission of photons is also possible, for example by the emission of a phonon). The dipole emission propagates symmetrically to the axis of the dipole moment wherein the intensity is at its maximum perpendicular to the dipole axis wherein it vanishes parallel to the dipole axis.

Accordingly, the emitted fluorescence light is polarized and anisotropic.

Figure 2:
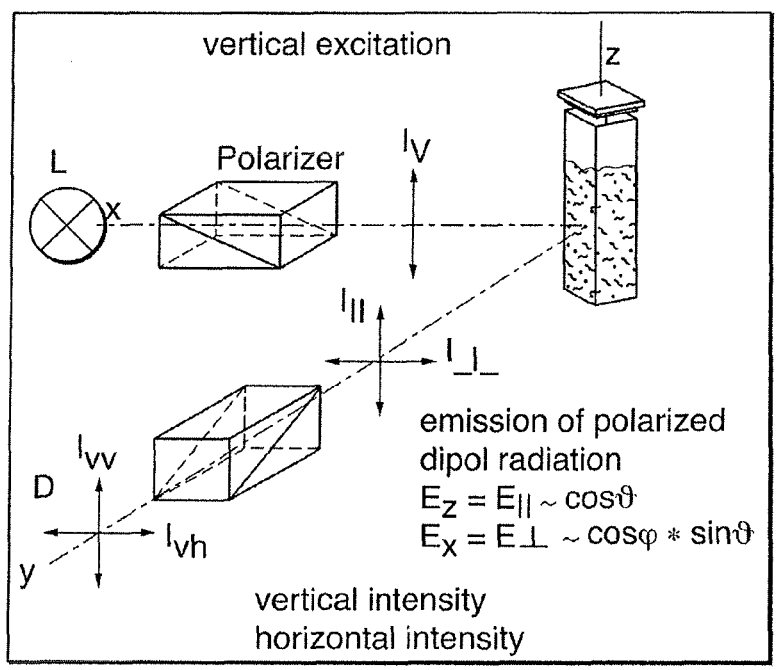
FIG. 2 shows a schematic experimental set-up for determining the anisotropy of the fluorophores in used dialysate.

FIG. 2 schematically shows an arrangement for measuring the excitation light as well as the emitted light. The excitation light is emitted by light source L and is polarized in the first polarizer such that the vector of the electrical field is perpendicular to the plane in which the excitation and the emission rays are located.

On the side of detector D, a second polarizer is provided which can be rotated and which is placed such that only the emitted fluorescence light is passed through. Preferably, the direction of the excitation light and the direction in which the detector D is arranged relative to the sample are perpendicular with respect to one another in order to avoid that the excitation light impinges on the detector.

By rotating the second polarizer, the intensities $I_{vv}$ (vertical intensity) and the intensity $I_{vh}$ (horizontal intensity) can be detected by the detector D. The difference of the intensities $I_{vv}-I_{vh}$ is a measure for the polarization of the light received at the detector D. The polarization P as well as the anisotropy A can be determined as follows:

$$P = \frac{I_{vv} - G*I_{vh}}{I_{vv} + G*I_{vh}} \quad (1)$$

$$A = \frac{I_{vv} - G*I_{vh}}{I_{vv} + 2*G*I_{vh}} \quad (2)$$

Here $I_{vh}$ is the detected intensity of the fluorescence light when the second polarizer is rotated such that only horizontally polarized light may pass. $I_{vv}$ is the detected intensity of the fluorescence light when the emission polarizer is rotated such that only vertically polarized light may pass. G is an apparatus constant which is provided in order to compensate for potential different sensitivities of the measurement system in the horizontal and the vertical planes. G is to be determined experimentally and may be put into the software of the system as a constant. The constant G can also be measured online by measuring the intensity of the light which passes through the polarizer in the horizontal polarization when using horizontally polarized excitation light and by measuring the intensity of the system in a vertical polarization when vertically polarized excitation light is used. The apparatus constant is then determined as $G=I_{hv}/I_{hh}$. $I_{vv}+2GI_{vh}$ is the average emission intensity if the total emitted power would be emitted isotropically over the total angle $\Omega=4\pi$.

As can be taken from equations (1) and (2), the polarization P and the anisotropy A can be easily substituted with respect to one another.

The anisotropy ranges between $-0.2 \leq A_0 \leq 0.4$. The maximum value of 0.4 corresponds to a collinear alignment of the absorption and emission transition dipole moments in the absence of any other depolarizing influences. In other words, it corresponds to $\alpha=0°$. However, in reality the absorption dipole moments as well as the emission dipole moments are typically not collinear but enclose an angle $\alpha$ with respect to one another. The detected anisotropy is then $$A_0 = \frac{3*\cos^2\alpha - 1}{5} \quad (3)$$

For $\alpha=0$, i.e. a collinear arrangement of the absorption dipole moment and the emission dipole moment, $A_0=0.4$ and for $\alpha=90°$ the value for $A_0=-0.2$. At the so-called magic angle of $\alpha=54.7°$ no anisotropy can be observed.

Because the orientation of the transition dipole moment varies depending on the absorption bands, the angle $\alpha$ and with it the anisotropy $A_0$ is also variable with the excitation wavelength $\lambda_{exc}$ and also with the emission wavelength $\lambda_{em}$. The function of anisotropy $A_0(\lambda_{exc}, \lambda_{em})$ is specific for every fluorophor, as is very schematically shown in FIG. 3.

Figure 3:
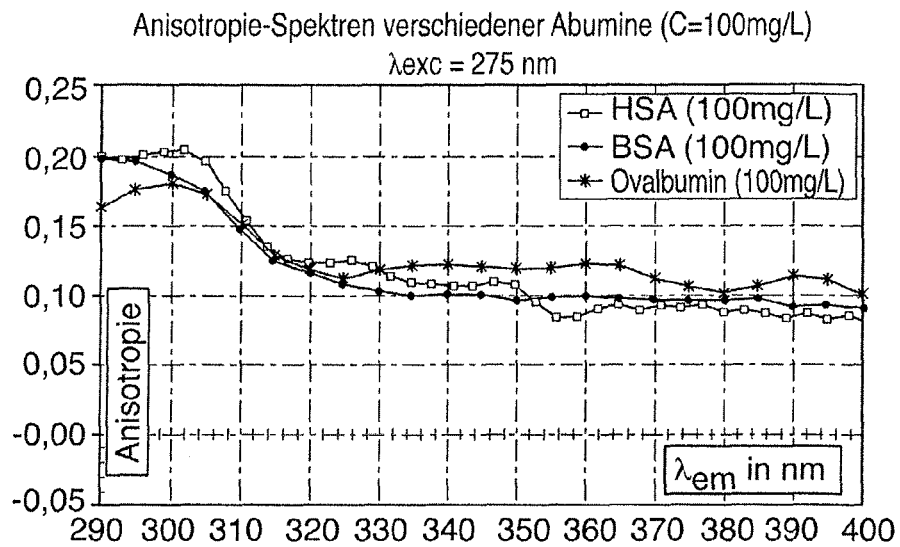
FIG. 3 shows schematic diagrams of anisotropy spectra of different molecules, in particular of human albumin and tryptophan.
Figure 3:
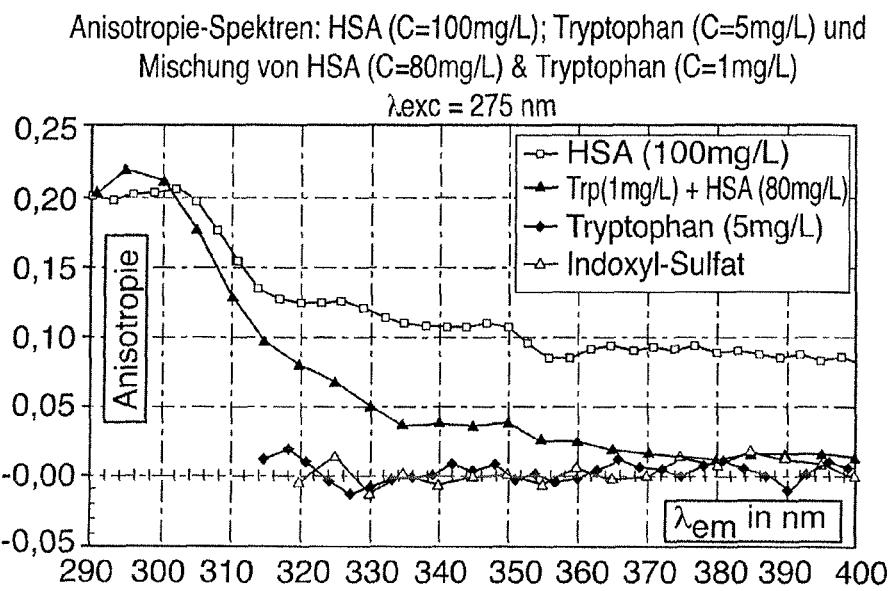

In particular, in FIG. 3 in the top diagram the anisotropy spectra of human albumin, bovine albumin and pure albumin are shown at an excitation wavelength of $\lambda_{exc}=275$ nm. It can be clearly seen that the anisotropy varies between 0.2 and 0.1 for different emission wavelengths $\lambda_{em}$ between 290 nm and 400 nm.

In the bottom diagram of FIG. 3, the anisotropy spectra of human albumin (66.5 kDa), of the amino acid tryptophan (204 Da), of a mixture of both substances, as well as of indoxyl sulfate is shown. Here, again, it can be clearly seen that the anisotropic function $A_0(\lambda_{exc}, \lambda_{em})$ is specific for each fluorophor.

Furthermore, the anisotropic function $A_0(\lambda_{exc}, \lambda_{em})$ is influenced by external factors such as the temperature and viscosity of the medium as well as the binding of the respective fluorophor to other media. This can also be seen when analyzing the lower diagram in FIG. 3 in which the anisotropic function of tryptophan is considerably different from that of a combination of tryptophan and human albumin.

An important consideration with respect to the analysis of used dialysates is provided in that only the larger molecules show significant anisotropies due to their relatively large rotation correlation time constant $\theta$, as will be discussed further below. These substances in the used dialysate are typically proteins, wherein albumin is an important representative of this species. The smaller molecular fluorophors typically provide only isotropically distributed intensities in the polarized intensities $I_{vv}$ and $I_{vh}$. Their specific anisotropies are, therefore, $A_j=0$. Accordingly, on the basis of this finding, the intensity proportion of albumin can be determined on the basis of the total anisotropy $A_{ges}$, provided the other fluorophores which are expected to be present in the dialysis fluid provide only isotropic contributions.

Figure 4:
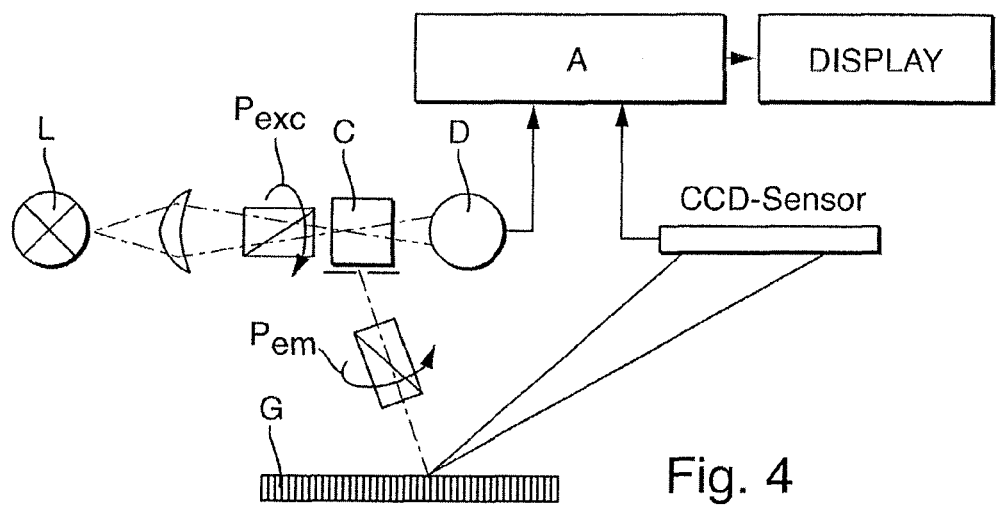
FIG. 4 is a schematic representation of an apparatus for carrying out the method suggested.

FIG. 4 schematically shows a measurement setup which can be used in combination with the present method. In particular, a light source L is provided which is collimated and focused by means of a lens and the excitation light is polarized by means of the polarizer $P_{exc}$. The polarized, collimated and focused excitation light is then directed into a cuvette C and is measured by means of a photodiode D in order to adjust for varying intensities of the light source L.

The fluorescence light emitted by the fluorophors in the cuvette C is extracted under an angle such that the emission light from light source L does not interfere with the fluorescence light. The fluorescence light is sent through a second polarizer $P_{em}$, which can be adjusted in its orientation. Then, the polarized fluorescence light impinges onto a diffraction grating G and is reflected onto a CCD-sensor such that the total spectrum of the fluorescence light can be analyzed in the analysis unit A. The results may be displayed in a display.

Because the used dialysate downstream of the dialyser typically includes more than one fluorophors, the absorption and emission spectra thereof are assumed to be superimposed. Accordingly, the total anisotropy $A_{ges}$ of the summarized spectra reads:

$$A_{ges} = \sum_i f_i * A_i \quad (4)$$

$$\text{wherein } f_i = \frac{S_i}{S_{ges}} = \frac{I_{vv,i} + 2*G*I_{vh,i}}{I_{vv,ges} + 2*G*I_{vh,ges}} \quad (5)$$

$A_{ges}$ is the anisotropy of the summarized spectra, $A_i$ is the anisotropy of the $i^{th}$ fluorophor, $f_i$ is the intensity fraction of the $i^{th}$ fluorophor with respect to the total intensity, $S_i$ is the total intensity of the physical radiation of the $i^{th}$ fluorophor, $S_{ges}$ is the total physical intensity of the radiation of all fluorophors $I_{vh,i}$ is the measured horizontal fluorescence intensity of the $i^{th}$ fluorophor, $I_{vv,i}$ is the measured vertical fluorescence intensity of the $i^{th}$ fluorophor, and i is the index over all fluorophors.

The total physical intensity of the physical radiation $S_i$ of a fluorophor is, provided it is sufficiently diluted, proportional to its concentration $C_i$. The anisotropies $A_i$ of the i fluorophores are assumed to be known constants. The intensity fractions $f_i$ have to be determined on the basis of the summarized spectrum.

As has been mentioned above, only larger molecules provide a significant proportion of the anisotropies. Accordingly, on the basis of equation (4) above, the intensity fraction of albumin $f_{alb}$ can be calculated on the basis of the measured total isotropy $A_{ges}$ even if the fluorescence fraction of albumin cannot be directly determined on the basis of the summarized spectrum:

$$f_{Alb} = \frac{A_{ges}}{A_{Alb}} \quad (6)$$

On this basis, the total physical intensity of the radiation of the albumin is given, on the basis of equation (5), as follows:

$$S_{Alb} = f_{Alb} * S_{ges} = \frac{A_{ges} * S_{ges}}{A_{Alb}} \quad (7)$$

On this basis, the concentration of albumin can be determined as follows:

$$C_{Alb} = \frac{1}{5} * \frac{g(\lambda)}{I_{exc,0}} * S_{Alb} \quad (8)$$

$$\text{where } g(\lambda) = \frac{10 * \varepsilon * \lambda_{em}^4}{\pi^2 * c * \Phi_e * \alpha(\lambda_{exc}) * L * p^2} \quad (9)$$

Wherein $I_{exc,0}$ is the intensity of the polarized irradiation light, $\varepsilon$ is the electrical field constant, $\lambda$ is a wavelength pair (irradiation $\lambda_{exc}$, emission $\lambda_{em}$), c is the speed of light, $\Phi_e$ is the quantum efficiency, $\alpha(\lambda_{exc})$ is the absorption coefficient at the irradiation wavelength $\lambda_{exc}$, L is the path through the cuvette, and p is the electrical dipol moment of the excited fluorophore.

The excitation intensity $I_{exc,0}$ may vary over time and is preferably measured online and corrected. The function $g(\lambda)$ can also be seen as a calibrating function which is determined experimentally on the basis of pure albumin or other reference solutions. The function $g(\lambda)$ may, for example, be determined at the manufacturer side of the respective apparatus.

As an aside, the intensity $I_{H2O,0}$ of the Stokes lines of the spectrum of water can be also determined such that in operation of the device the actual intensity $I_{H2O}$ may be measured and the calibration function $g(\lambda)$ can be adjusted to the actual state of the apparatus:

$$g(\lambda) = g_0(\lambda) * I_{H2O}/I_{H2O,0}$$

On this basis, cost-effective cuvettes with relatively large mechanical tolerances may be used for determining the concentrations of the fluorophores.

If the polarized radiation components $S_x$ and $S_z$ are overlapped by isotropic radiation of other fluorophors, in particular, by the isotropic radiation of smaller molecules which have, as has been discussed above, only a limited—if any—influence on the anisotropy of the measured radiation intensities, the isotropic components provide the same offset $S_{offset}$ to both polarized radiation components $S_x$ and $S_z$ $$S_{x,ges} = S_{x,Alb} + S_{offset} \quad (10a)$$

$$S_{z,ges} = S_{z,Alb} + S_{offset} \quad (10b)$$

Accordingly, the intensity of the radiation of the albumin can be easily determined by simple subtraction (under the assumption that it is only the human albumbin that shows a significant anisotropy):

$$\Delta S_{Alb} = S_{z,Alb} - S_{x,Alb} = S_{z,ges} - S_{x,ges} = I_{vv,ges} - G * I_{vh,ges} \quad (11)$$

$$\Delta S_{ges} = 3 * \frac{I_{exc,0}}{g(\lambda)} * C_{Alb} - \frac{I_{exc,0}}{g(\lambda)} * C_{Alb} = 2 * \frac{I_{exc,0}}{g(\lambda)} * C_{Alb}$$

$$C_{Alb} = \frac{1}{2} * g(\lambda) * \frac{I_{vv,ges} - G * I_{vh,ges}}{I_{exc,0}} \quad (12)$$

Where $I_{vh,i}$ is the detected total horizontal fluorescence intensity and $I_{vv,i}$ is the detected total vertical fluorescence intensity.

Figure 5:
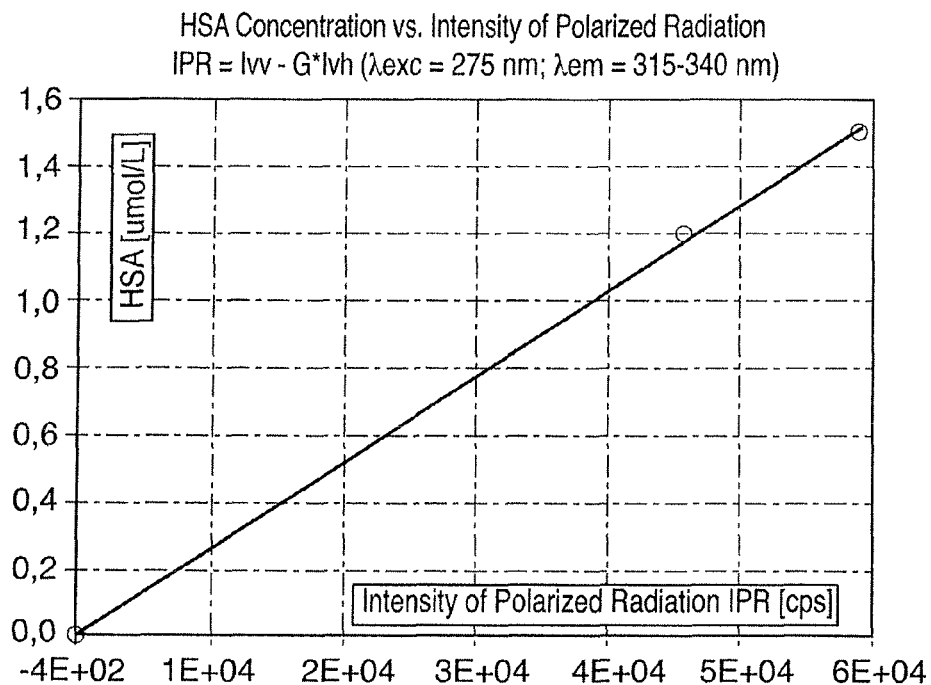
FIG. 5 is a schematic diagram representing the concentration of human albumin as a function of the measured intensity of the total polarized fluorescence light.

FIG. 5 shows, in a schematic diagram, the concentration of human serum albumin (HAS) as a function of the measured intensity of the total polarized fluorescence radiation for different mixtures of HAS and free tryptophan.

The different fluorophors may be distinguished with respect to the molecular sizes. In this respect, the following considerations are of interest:

The absorption of the exciting photon takes only about $10^{-15}$ sec. By means of relaxation with the molecule vibrations, in other words, by means of internal conversion, the excited state $S_1$ relaxes very quickly, typically within $10^{-12}$ sec, to the energetically lowest possible vibrational level, because the lifetime of the fluorescence is in the range of $\tau = 10^{-8}$ sec and is, thus, substantially longer.

From this energetically lowest vibrational level, the excited electron relaxes into the ground state $S_0$ either by emission of a photon or by means of a radiation transition. Both processes depopulate the excited state $S_1$. Accordingly, if the sample is excited by means of a short excitation impulse, the fluorescence intensity I shows the following decay function:

$$I = I_0 * e^{-t/\tau} \quad (13)$$

wherein $\tau$ is the lifetime of the excited state.

With respect to the anisotropy A, another mechanism adds to the depolarization of the intensity, because the molecules rotate around their axis, which is connected to the direction of emission. Immediately after the exciting impulse all molecules are synchronized but after this impulse, all diffuse during a characteristic time span, which is termed the rotation correlation time $\theta$. For freely rotating, spherical molecules the Perrin relation is given:

$$A = A_0 * e^{-t/\theta} \quad (14)$$

Wherein $\theta$ is the rotation correlation time, which is a characteristic time constant describing the time period within which the axis of the transition dipole moments are oriented diffusely by means of rotation of the molecules, and $A_0$ is the anisotropy at the time t=0, before any depolarizing effects occur.

At a pulsed excitation, the decay of the anisotropy according to equation (14) can be observed in a time-resolved manner. On this basis, the rotation correlation time $\theta$—or by superposition of more than one fluorescence signals the rotation correlation times of the individual fluorophores $\theta_i$—may be determined, wherein the rotation correlation time $\theta$ is specific for each fluorophor. Accordingly, the determined rotation correlation time $\theta$ is indicative for the individual fluorophores.

When continuously irradiating the sample, the following value of the anisotropy $A_m$ can be determined:

$$\int_0^\infty A_m * e^{-t/\tau} * dt = \int_0^\infty A_0 * e^{-t/\theta} * e^{-t/\tau} * dt \quad (15)$$

$$A_m * \int_0^\infty e^{-t/\tau} * dt = A_0 * \int_0^\infty e^{-t*(1/\theta + 1/\tau)} dt$$

$$A_m * \tau = A_0 * \frac{1}{\frac{1}{\theta} + \frac{1}{\tau}}$$

$$\frac{A_m}{A_0} = \frac{1}{1 + \frac{\tau}{\theta}}$$

For calculating the correlation time constant $\theta$ of spherical molecules more often, the following correlation is used:

$$\theta = \frac{\eta * M}{R * T} * (\bar{v} + h) \quad (16)$$

Wherein $\eta$ represents the viscosity of the solvent at a temperature T[Pa*s], M is the molar mass of the molecule [g/mol], R is the general gas constant [8,314 J/mol/K], T is the temperature [K], $\bar{v}$ is the specific volume of the molecule [ml/g], for example proteins: 0.73 ml/g, and h is the hydration [ml/g]], (for example for proteins: 0.32 ml/g)

For smaller molecules in lower viscous solvents (for example in water or in plasma) the anisotropy decays very quickly, wherein for larger molecules, for example proteins, the anisotropy is maintained for a relatively long timespan and may even exceed the fluorescence lifetime $\tau$.

Figure 6:
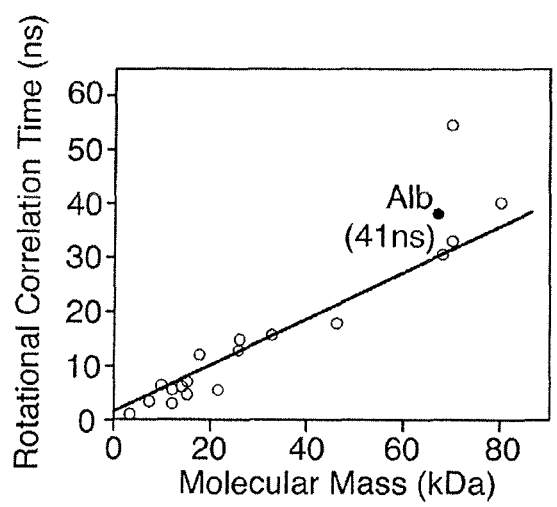
FIG. 6 is a schematic diagram showing the correlation time constants for proteins of different molecular mass.

In FIG. 6 different measurements of different proteins of different molecular mass are shown, for example albumin (66 kDa), and of lighter proteins such as, for example, β2m (11.7 kDa), and even for smaller molecules such as, for example, free tryptophan (<0.5 kDa), which can be distinguished by means of the correlation time constant $\theta$ (Ref.: Joseph R. Lakowicz, Topics in the Fluorescence Spectroscopy, Volume 6, Protein Fluorescence, ISBN: 0-306-46451-9, 2002 Kluwer Academic Published, New York, Boston, Dordrecht, London, Moskow).

According to equation (15), the average anisotropy $A_m$ varies with the correlation time constant $\theta$ and, thus, with the molecular mass M, as can be taken from equation (16).

By the application of lower temperatures such as by cooling down the sample, or by raising the viscosity by means of, for example, gel building or freezing, the lifetime of the anisotropy may be prolonged.

The orientations of the molecular axes, which are typically statistically evenly distributed in space, may be aligned by means of the application of an external electrical or magnetical field, which acts on their respective electrical or magnetical dipole moment. By means of this measure, the excitation in an optimally aligned polarization plane can be increased such that the signal intensity of the process can be improved. Furthermore, the free rotation of the molecules might be hindered such that the lifetime of the anisotropy may be prolonged.

On this basis, a clear distinction between the molecules can be achieved.

For example, for free tryptophan, molecules a fluorescence lifetime of $\tau=3$ ns and a correlation time constant of $\theta=50$ picosecond are provided such that $A_m/A_0=1.6\%$. For tryptophan molecules which are bound to human albumin, however, the fluorescence lifetime is $\tau=8$ ns and the correlation time constant is $\theta=41$ nsec, such that $A_m/A_0=83.7\%$.

In used dialysate the anisotropy spectrum contains, in general, a superposition of intensity portions of different middle molecular substances and even other fluorophors. On the basis of this measured total spectrum, the anisotropy proportions of the individual substances need to be calculated in order to determine the individual concentrations of the individual substances.

By means of the following method, the measured spectrum $f(\lambda)$ is seen as a linear opposition of the spectra of N different fluorophors:

$$f(\lambda) = \sum_{i=1}^{N} c_i s_i(\lambda)$$

Here, $c_i$ is the concentration of the i-th fluorophore and $s_i(\lambda)$ is the sensitivity.

If the spectrum is measured at M different pairs of wavelength $\lambda_i(\lambda_{i,exc}, \lambda_{i,em})$, an equation system of m equations with n unknowns is achieved:

$$\begin{pmatrix} f(\lambda_1) \\ f(\lambda_2) \\ \vdots \\ f(\lambda_M) \end{pmatrix} = \begin{pmatrix} s_1(\lambda_1) & s_2(\lambda_1) & \cdots & s_N(\lambda_1) \\ s_1(\lambda_2) & s_2(\lambda_2) & \cdots & s_N(\lambda_2) \\ \vdots & \vdots & \ddots & \vdots \\ s_1(\lambda_M) & s_2(\lambda_M) & \cdots & s_N(\lambda_M) \end{pmatrix} \begin{pmatrix} c_1 \\ c_2 \\ \vdots \\ c_N \end{pmatrix}$$

The solution of the above-mentioned system of equations can be provided, most practically, by means of a least square fit:

$$S = \sum_{i=1}^{M} \left( f(\lambda_i) - \sum_{j=1}^{N} s_j(\lambda_i) c_j \right)^2$$

Accordingly, the concentrations $c_j$ are the coefficients in the linear equation system, wherein the k-th concentration $c_k$ can be calculated by means of the determinant det( ) as follows:

$$c_k = \frac{\det(\vec{x}_1, \vec{x}_2, \ldots, \vec{x}_{k-1}, \vec{y}, \vec{x}_{k+1}, \ldots, \vec{x}_N)}{\det(\vec{x}_1, \vec{x}_2, \ldots, \vec{x}_N)}$$

Figure 7:
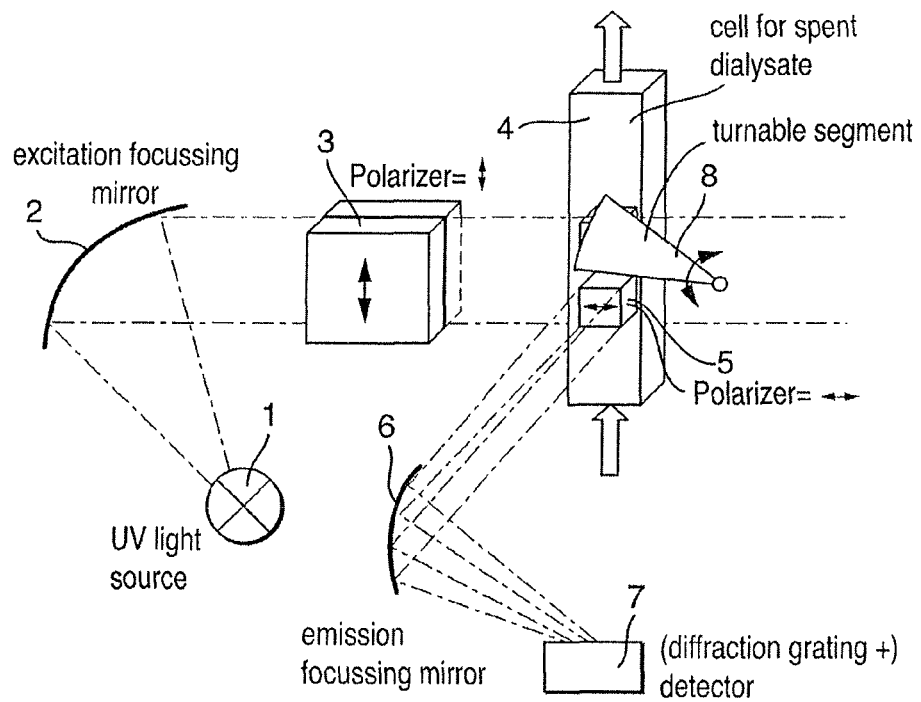
FIG. 7 is a schematic representation of an experimental setup for measuring the anisotropy in UV-light, wherein the intensity of polarized light is measured in the horizontal plane.
Figure 8:
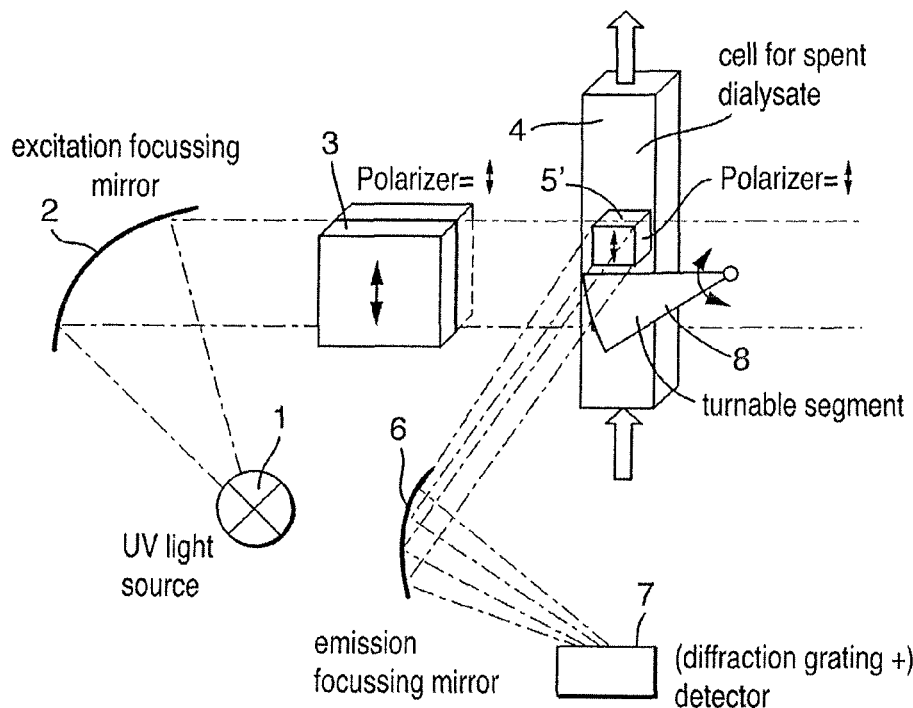
FIG. 8 corresponds to the schematic representation of FIG. 7 but with a different polarizer such that the intensity of polarized light is measured in the vertical plane.

FIG. 7 and FIG. 8 show examples of a setup of a measurement apparatus for carrying out the method. A UV irradiation light source 1 is provided which is used for providing the excitation light. The UV light source 1 can be provided as a narrow emitting LED, as a laser or also as a broadly emitting light source such as a Hg, Xe or Deuterium lamp which would then be used in connection with a monochromator or any other optical band pass such as a Fabry-Perrot filter.

The excitation light emitted from the light source 1 is focused by means of a focusing mirror 2. The focusing mirror 2 serves to focus and/or collimate the light of the UV light source 1. The focused and/or collimated light is then guided through a polarizer 3 which is, most preferably, a fixed polarizer. The fixed polarizer is intended to polarize the light vertically ($I_v$). The vertically polarized light is then guided through the cuvette 4 in which the dialysis fluid in form of the used dialysate flows.

An apparatus constant $G(\lambda)$ can be determined at the manufacturer's side by means of manually rotating the polarizer 3 by 90° such that the intensities for the vertical polarization and the horizontal polarization can be reliably measured.

In the cuvette 4 through which the used dialysate flows, the polarized excitation light impinges upon the fluorophors to excite them. The fluorescence light emitted from the excited fluorophors is then guided through a first polarizer 5 and then—by means of an emission focusing mirror 6—onto a diffraction grating and to detector 7 in order to determine the actual fluorescence spectrum.

The polarizer 5 is arranged as a horizontal polarizer in FIG. 7. In FIG. 8, a second polarizer 5' is present which is arranged as a vertical polarizer.

As can be seen in comparison with FIG. 8, a turnable shutter segment 8 is provided, which shuts either the first polarizer 5 or the second polarizer 5' such that by means of the turnable shutter segment 8, the fluorescence light detected by the detector 7 can be selected between a horizontal polarization (as in FIG. 7) and a vertical polarization (as in FIG. 8).

Furthermore, in the emission path of light, the first horizontal polarizer 5 and the second vertical polarizer 5' are fixedly built into the device such that the optical parts cannot become misaligned and the apparatus constant G can be determined reliably. The advantage of the rigid arrangements of the polarizers shown is that the optical components do not have to be moved in operation. Accordingly, tolerances on the basis of mechanical reproductions are not present.

Figure 9:
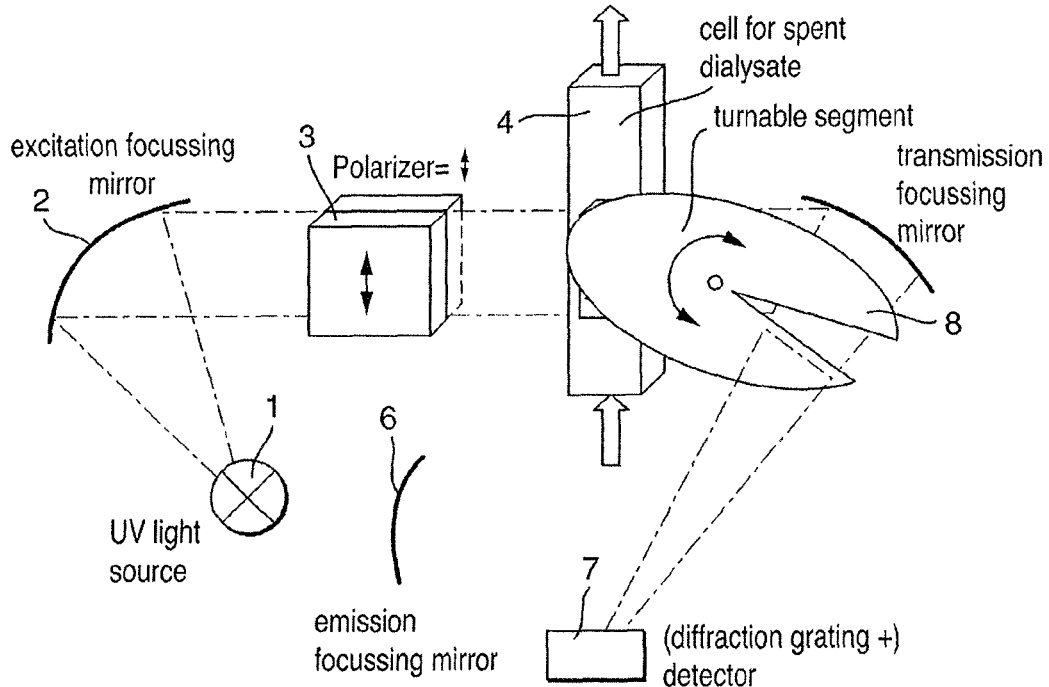
FIG. 9 shows an alternative arrangement of an experimental setup for measuring UV anisotropie.

FIG. 9 suggests using, in a similar arrangement, another turnable segment in form of a rotating aperture which is located in a path of light stemming from the transmission side of the cuvette such that the exciting light transmitted through the cuvette can be measured with the same detector 7 as the two differently polarized fluorescence lights. In particular, the intensity of the polarization $I_{vv}$, the intensity of the polarization $I_{vh}$, the intensity of the transmission $I_t$ as well as the background intensity of the shut-off detector $I_d$ can be measured with this setup and with a single detector 7.

Figure 10:
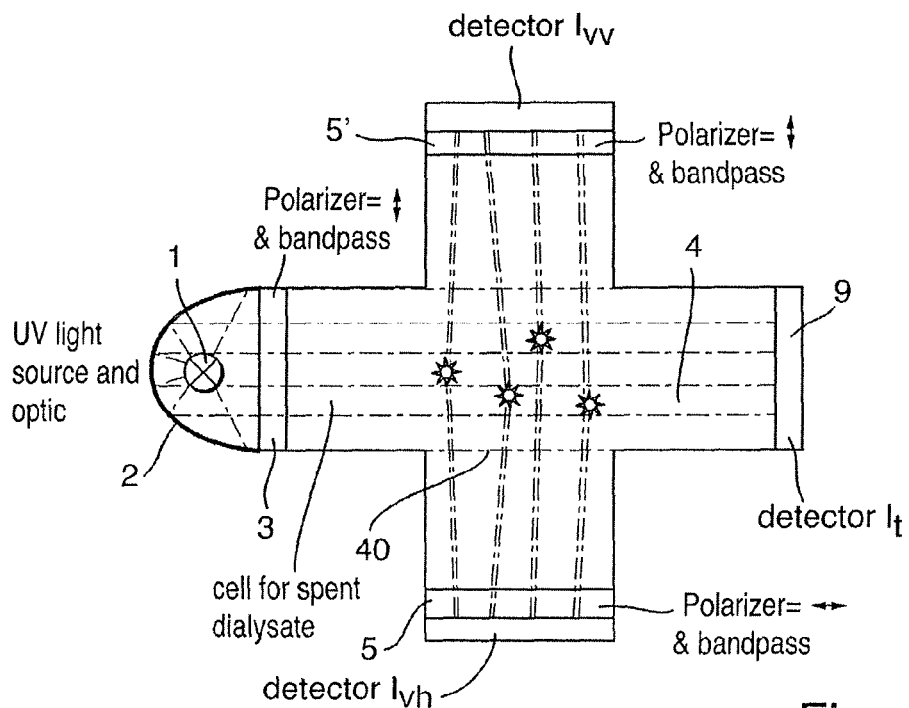
FIG. 10 shows yet another alternative arrangement of an experimental setup for measuring the UV anisotropy.

In FIG. 10 another arrangement is shown, according to which the intensities of the two different polarizations as well as the transmission intensity can be measured at the same time. In particular, the T-shaped arrangement of the two polarizers 5 and 5' with associated detectors for detecting the polarized fluorescence intensities $I_{vv}$ and $I_{vh}$, as well as a third detector 9 for detecting the transmission intensity $I_t$ is present.

The vertical polarizer 5 is provided on one side of the cuvette 4 and the horizontal polarizer 5 is provided on the opposite side of the cuvette 4, such that the light is either coupled out on the one hand side or on the other hand side, resulting in a T-shaped arrangement. This has the advantage that the surface for coupling the emitted fluorescence light out of the cuvette 4 can be enlarged such that the sensitivity can be increased. Furthermore, with the mentioned arrangement in which the light is coupled out at two different sides of the cuvette through polarizers which are oriented with respect to one another by 90°, and the two intensities can be analyzed at the same time.

In order to couple the light out of the cuvette 4, specific windows 40 may be provided in order to avoid reflections.

The invention claimed is:

1. Method for monitoring an extracorporeal blood treatment of a patient, wherein the extracorporeal blood treatment is dialysis, haemodialysis, haemodiafiltration, or haemofiltration, comprising during the extracorporeal blood treatment the steps of:
   irradiating a sample of a treatment fluid used in and taken during the extracorporeal blood treatment with linearly polarized irradiation light;
   detecting the intensity of the fluorescence light emitted by the sample of the used treatment fluid in a first polarization plane;
   detecting the intensity of the fluorescence light emitted by the sample of the used treatment fluid in a second polarization plane which is different from the first polarization plane;
   determining the anisotropy of the fluorescence light emitted by the sample of the used treatment fluid from the detected intensity in the first polarization plane and the detected intensity in the second polarization plane; and
   determining the concentration of at least one fluorophore in the sample of the used treatment fluid based on at least one of the determined anisotropy and the detected intensities of the fluorescence light emitted by the sample of the used treatment fluid.

2. The method according to claim 1, wherein the first polarization plane and the second polarization plane are oriented perpendicular with respect to one another and the anisotropy A is determined on the basis of the following equation $$A = \frac{I_{vv} - G * I_{vh}}{I_{vv} + 2 * G * I_{vh}}$$

where $I_{vv}$ is the intensity of the detected fluorescence light in the vertical polarization plane, $I_{vh}$ is the intensity of the detected fluorescence light in the horizontal polarization plane, and G is an apparatus constant compensating differences in the sensitivities of the apparatus when detecting intensities in the first and second polarization planes.

3. The method according to claim 2, wherein the intensity of the fluorescence light is detected at a predetermined detection wavelength when irradiating the sample of the used treatment fluid at a predetermined irradiation wavelength, the determined anisotropy is used to identify a fluorophore in the sample, and the detected intensities of the fluorescence light are used to determine the concentration of the identified fluorophore, wherein the anisotropy of specific individual fluorophores is known.

4. The method according to claim 2, wherein the concentrations of at least two fluorophores present in the sample of the used treatment fluid are determined on the basis of the following equation of the total anisotropy $A_{total}$ of the summed spectra:

$$A_{total} = \sum_i f_i * A_i$$

wherein $f_i = \dfrac{S_i}{S_{total}} = \dfrac{I_{vv,i} + 2*G*I_{vh,i}}{I_{vv,total} + 2*G*I_{vh,total}}$ and wherein $A_{total}$ is the total anisotropy of the summed spectra, $A_i$ is the anisotropy of the $i^{th}$ fluorophor, $f_i$ is the intensity fraction of the $i^{th}$ fluorophore with respect to the total intensity, $S_i$ is the total intensity of the physical radiation of the $i^{th}$ fluorophore, $S_{total}$ is the total intensity of the physical radiation of all fluorophors, $I_{vh,i}$ is the detected horizontal fluorescence intensity of the $i^{th}$ fluorophor, $I_{vv,i}$ is the detected vertical fluorescence intensity of the $i^{th}$ fluorophor, $I_{vh,total}$ is the total detected horizontal fluorescence intensity of all fluorophores, $I_{vv,total}$ is the total detected vertical fluorescence intensity of all fluorophores, and i is the index over all fluorophors, and wherein the anisotropy $A_i$ of the $i^{th}$ fluorophor is known.

5. The method according to claim 4, wherein the concentration of the at least one fluorophore is determined based on the total anisotropy.

6. The method according to claim 4, wherein a matrix decomposition of the determined anisotropy spectrum is carried out and a comparison to known anisotropy spectra of known substances is carried out in order to determine on the basis of the respective intensities of the known substances their respective concentrations.

7. The method according to claim 2, wherein the concentration of the at least one fluorophore is determined based on the vertical and horizontal intensities of the detected fluorescence light.

8. The method according to claim 2, wherein the sample of the used treatment fluid is irradiated with pulsed linearly polarized irradiation light and the detection of the fluorescence light in the first and second polarization planes is carried out in a time-resolved fashion and $$A = A_0 * e^{-t/\theta}$$

where $\theta$ is the rotation correlation time, which is a characteristic time constant describing the time period within which the axis of the transition dipole moments are oriented diffusely by rotation of the molecules, and $A_0$ is the anisotropy at the time point t=0, before depolarizing effects apply.

9. The method according to claim 8, wherein the rotation correlation time is varied by at least one of varying the temperature of the sample of the used treatment fluid, varying the viscosity of the sample of the used treatment fluid, applying an external magnetic field to the sample of the used treatment fluid, and applying an external electrical field to the sample of the used treatment fluid.

10. The method according to claim 8, wherein the total fluorescence intensity is increased by aligning the transition dipole moments of the sample of the used treatment fluid by applying to the sample at least one of external electrical and magnetic fields.

11. The method according to claim 2, wherein the at least one fluorophore is human albumin and the concentration of human albumin in the irradiated sample is determined based on subtraction from the detected horizontal intensity of the detected vertical intensity.

12. The method according to claim 1, wherein a sample of the used treatment fluid is taken continuously, irradiated, and the detection is continuously carried out.

13. The method according to claim 1 further comprising the steps of:

irradiating a sample of fresh treatment fluid to be used in the extracorporeal blood treatment with linearly polarized irradiation light;
detecting the intensity of the fluorescence light emitted by the sample of the fresh treatment fluid in a first polarization plane;
detecting the intensity of the fluorescence light emitted by the sample of the fresh treatment fluid in a second polarization plane which is different from the first polarization plane;
determining the anisotropy of the fluorescence light emitted by the sample of the fresh treatment fluid; and
determining the concentration of the at least one fluorophore in the sample of the fresh treatment fluid on the basis of, both, the determined anisotropy and the intensities of the fluorescence light emitted by the sample of fresh treatment fluid;
whereby, based on the determined concentration of the at least one fluorophore in the sample of fresh treatment fluid, the contribution of contaminations of the fresh-dialysis treatment fluid to the determined concentration of the fluorophore in the sample of the used treatment fluid taken during the extracorporeal blood treatment can be eliminated.

14. Device for monitoring an extracorporeal blood treatment of a patient according to the method of claim 1 and comprising an irradiation light source for irradiating the sample of used treatment fluid with linearly polarized light, first and second detectors for detecting the intensity of the fluorescence light emitted by the sample of the used treatment fluid in a first polarization plane and in a second polarization plane which is different from the first polarization plane, and a third detector present collinearly with the irradiation light and such that the sample of the used treatment fluid is placed between the third detector and the irradiation light source to detect a transmission intensity, wherein an analysis unit is present for determining the anisotropy of the fluorescence light emitted by the sample of the used treatment fluid from the detected intensity in the first polarization plane and the detected intensity in the second polarization plane and for determining the concentration of at least one fluorophore in the sample of the used treatment fluid on the basis of the determined anisotropy and the intensity of the fluorescence light emitted by the sample of the used treatment fluid.

15. Device for monitoring an extracorporeal blood treatment of a patient, wherein the extracorporeal blood treatment is dialysis, haemodialysis, haemodiafiltration, or haemofiltration, comprising an irradiation light source for irradiating a sample of treatment fluid used in the dialysis treatment with linearly polarized light, at least one detector for detecting the intensity of the fluorescence light emitted by the sample of the used treatment fluid in a first polarization plane and in a second polarization plane which is different from the first polarization plane, and an analysis unit for determining the anisotropy of the fluorescence light emitted by the sample of the used treatment fluid from the detected intensity in the first polarization plane and the detected intensity in the second polarization plane and for determining the concentration of at least one fluorophore in the sample of the used treatment fluid based on at least one of the determined anisotropy and the intensities of the fluorescence light emitted by the sample of the used treatment fluid.

16. Device according to claim 15 further comprising at least two polarizers, with polarization planes aligned under an angle, provided between the sample of the used treatment fluid and the detector and a movable shutter present in the light path to alternately cover either of the two polarizers to alternately detect the intensities of the fluorescence light in the two polarization planes.

17. Device according to claim 16 further comprising a rotatable shutter present in the light path of the transmitted light of the light source through the sample of the used treatment fluid wherein the intensity of the transmitted light as well as the intensities of the fluorescence light in at least two different polarization planes can be detected by a single detector.

18. Device according to claim 15, wherein the at least one detector is a first detector with an associated polarizer with a first polarization plane and a second detector with an associated polarizer with a second polarization plane different from the first polarization plane arranged on opposite sides of the sample of the used treatment fluid to detect fluorescence light of a first and a second polarization plane simultaneously.

19. Device according to claim 18 further comprising a third detector present collinearly with the irradiation light and such that the sample of the used treatment fluid is placed between the third detector and the irradiation light source to detect the transmission intensity.

20. A method for monitoring protein concentration in a fluid used in extracorporeal blood treatment of a patient comprising the steps of
  irradiating a sample of the used treatment fluid taken during the extracorporeal blood treatment with linearly polarized irradiation light,
  detecting the intensity of the fluorescence light emitted by the sample of the used treatment fluid in a first polarization plane,
  detecting the intensity of the fluorescence light emitted by the sample of the used treatment fluid in a second polarization plane which is different from the first polarization plane,
  determining the anisotropy of the fluorescence light emitted by the sample of the used treatment fluid from the detected intensity in the first polarization plane and the detected intensity in the second polarization plane,
  determining the concentration of albumin in the sample of the fluid based on at least one of the determined anisotropy and the detected intensities of the fluorescence light emitted by the sample of the used treatment fluid, and
  adjusting the extracorporeal blood treatment based in the determined concentration of albumin, if necessary.

* * * * *